United States Patent
Matsumoto et al.

(10) Patent No.: US 10,150,857 B2
(45) Date of Patent: Dec. 11, 2018

(54) PHOSPHOROUS ACID COMPOUND, METHOD FOR PRODUCING SAID COMPOUND, AND USE OF SAID COMPOUND

(71) Applicant: SUMITOMO CHEMICAL COMPANY, LIMITED, Tokyo (JP)

(72) Inventors: Shuhei Matsumoto, Niihama (JP); Natsuko Kimura, Osaka (JP)

(73) Assignee: SUMITOMO CHEMICAL COMPANY, LIMITED, Chuo-ku, Tokyo (JP)

(*) Notice: Subject to any disclaimer, the term of this patent is extended or adjusted under 35 U.S.C. 154(b) by 0 days.

(21) Appl. No.: 15/548,796

(22) PCT Filed: Feb. 5, 2016

(86) PCT No.: PCT/JP2016/053474
§ 371 (c)(1),
(2) Date: Aug. 4, 2017

(87) PCT Pub. No.: WO2016/129517
PCT Pub. Date: Aug. 18, 2016

(65) Prior Publication Data
US 2018/0016417 A1    Jan. 18, 2018

(30) Foreign Application Priority Data
Feb. 12, 2015 (JP) ................ 2015-025727

(51) Int. Cl.
| | |
|---|---|
| *C07F 9/141* | (2006.01) |
| *C08L 23/00* | (2006.01) |
| *C08K 5/524* | (2006.01) |
| *C08K 5/51* | (2006.01) |
| *C09K 15/32* | (2006.01) |
| *C08L 101/00* | (2006.01) |
| *C07F 9/145* | (2006.01) |
| *C09K 15/08* | (2006.01) |

(52) U.S. Cl.
CPC ............... *C08K 5/51* (2013.01); *C07F 9/141* (2013.01); *C07F 9/145* (2013.01); *C08L 23/00* (2013.01); *C08L 101/00* (2013.01); *C09K 15/08* (2013.01); *C09K 15/32* (2013.01)

(58) Field of Classification Search
CPC ....... C07F 9/141; C07F 9/1411; C07F 9/1414
See application file for complete search history.

(56) References Cited

U.S. PATENT DOCUMENTS

| | | | |
|---|---|---|---|
| 3,542,724 A * | 11/1970 | Mirviss ................ | C08K 5/38 252/400.24 |
| 3,763,287 A * | 10/1973 | Chiddix et al. ......... | C07F 9/02 252/400.21 |
| 4,132,702 A * | 1/1979 | Schmidt ................ | C07C 215/54 252/400.2 |
| 4,333,868 A * | 6/1982 | Schmidt ................ | C07C 215/54 524/152 |
| 4,467,061 A | 8/1984 | Yamamoto et al. | |

FOREIGN PATENT DOCUMENTS

| | | |
|---|---|---|
| EP | 0823435 A2 | 2/1998 |
| GB | 1504573 A | 3/1978 |
| JP | 45129 B | 1/1970 |
| JP | 4638342 B | 11/1971 |
| JP | 50134987 A | 10/1975 |
| JP | 586084 A | 4/1993 |
| JP | 3876479 B2 | 1/2007 |
| WO | 2010/103023 A1 | 9/2010 |

OTHER PUBLICATIONS

Computer-generated English-language translation of RU-2665039 C1.*
Communication dated Jun. 29, 2018 from the Intellectual Property Office of Singapore in counterpart application No. 11201706164W.
Mousa Ghaemy et al., "Synergistic Effects of Some Phosphites Antioxidants Used in Polypropylene Stabilization," Iranian Polymer Journal; vol. 8, No. 1 (1999) 9 pages total.
Dr. H. Muller, "Polyolefin articles sterisable by gamma-irradiation," Research Disclosure; Feb. 1981; vol. 202 (abstract only) 2 pages total.

(Continued)

*Primary Examiner* — Vu A Nguyen
(74) *Attorney, Agent, or Firm* — Sughrue Mion, PLLC

(57) ABSTRACT

The present invention relates to a phosphorous acid compound represented by formula (I):

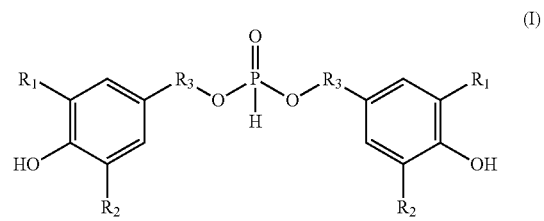

wherein $R_1$ represents a $C_{1-8}$ alkyl group, a $C_{5-8}$ cycloalkyl group, a $C_{6-12}$ alkyl cycloalkyl group, a $C_{7-12}$ aralkyl group or a $C_{6-12}$ aryl group; $R_2$ represents a hydrogen atom or a $C_{1-3}$ alkyl group; and $R_3$ represents a $C_{3-25}$ alkylene group, a stabilizer for organic materials containing the phosphorous acid compound, a method for stabilizing an organic material in which the phosphorous acid compound is added to the organic material, and a stabilized organic material composition containing an organic material and the phosphorous acid ester compound.

11 Claims, No Drawings

(56) References Cited

OTHER PUBLICATIONS

International Search Report, issued by International Searching Authority in corresponding International Application No. PCT/JP2016/053474, dated Apr. 26, 2016.
International Preliminary Report on Patentability and Written Opinion issued from the International Bureau in counterpart International Application No. PCT/JP2016/053474, dated Aug. 15, 2017.
Communication dated Mar. 6, 2018, from the Japanese Patent Office in counterpart application No. 2015-025727.
XP002782474, Abstract of Mousa Ghaemy et al., "Synergistic Effects of Some Phosphites Antioxidants Used in Polypropylene Stabilization," Iranian Polymer Journal; vol. 8, No. 1 (1999), (of record), 1 page total.
Communication dated Aug. 21, 2018 from the European Patent Office in counterpart Application No. 16749161.2.

* cited by examiner

PHOSPHOROUS ACID COMPOUND, METHOD FOR PRODUCING SAID COMPOUND, AND USE OF SAID COMPOUND

TECHNICAL FIELD

The present application claims priority of Japanese Patent Application No. 2015-025727 (filing date: Feb. 12, 2015), the entire contents of which are hereby incorporated by reference.

The present invention relates to a novel phosphorous acid compound, a method for producing said compound, and use of said compound as a stabilizer for organic materials.

BACKGROUND ART

It is known that organic materials such as thermoplastic resins, thermosetting resins, natural or synthetic rubbers, mineral oils, lubricants, adhesives, and paints are deteriorated through the action of heat, oxygen or the like during production or use, which are accompanied by deterioration in strength and physical properties, changes in flowability, coloring, and deterioration in surface physical properties of the organic materials attributable to phenomena including molecular cleavage and molecular crosslinkage, resulting in great impairment of their commercial values.

In order to prevent deterioration by heat or oxygen, various phenol antioxidants and various phosphorus antioxidants have been developed in the past. It has been known that organic materials can be stabilized by adding them to the organic materials. However, phosphorus acid antioxidants conventionally used may sometimes have an insufficient effect on deterioration by heat or oxygen and therefore compounds having a more stabilizing effect have been desired.

As a material which solves the problem of phosphorus antioxidants, cyclic phosphites having a carbonyloxyalkylene group are proposed (Patent Document 1). Although stabilizing effects by cyclic phosphites have been improved compared with those by phosphorus antioxidants, they were not satisfactory.

Furthermore, cyclic phosphorous acid esters whose stabilizing effects against deterioration by heat or oxygen have been more improved are also proposed (Patent Document 2).
Patent Document 1: JP H05-86084 A
Patent Document 2: JP 3876479 B

SUMMARY OF INVENTION

Problem to be Solved by the Invention

It is an object of the present invention to provide a novel compound which is superior in improvement of heat stability and oxidation stability of organic materials.

Means for Solving the Problem

The present inventors intensively studied in detail in order to solve the above problem, and found a novel phosphorous acid compound, thereby completing the present invention.

That is, the present invention includes the following preferred embodiments.
[1] A phosphorous acid compound represented by formula (I):

[Chemical Formula 1]

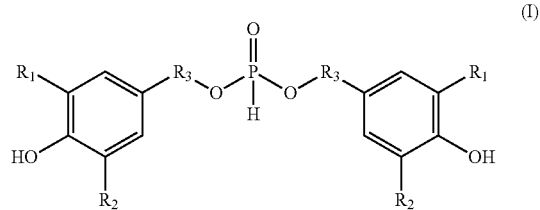

wherein $R_1$ represents a $C_{1-8}$ alkyl group, a $C_{5-8}$ cycloalkyl group, a $C_{6-12}$ alkyl cycloalkyl group, a $C_{7-12}$ aralkyl group or a $C_{6-12}$ aryl group; $R_2$ represents a hydrogen atom or a $C_{1-3}$ alkyl group; and $R_3$ represents a $C_{3-25}$ alkylene group.
[2] A method for producing the phosphorous acid compound according to the above [1] by reacting a phenol compound represented by formula (II):

[Chemical Formula 2]

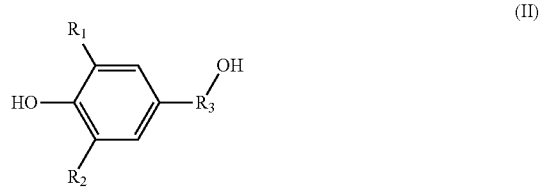

wherein $R_1$, $R_2$, and $R_3$ are as defined above, with a phosphorus trihalide.
[3] A stabilizer for an organic material, containing the phosphorous compound according to the above [1].
[4] The stabilizer according to the above [3], wherein the organic material is a thermoplastic resin.
[5] The stabilizer according to the above [4], wherein the thermoplastic resin is a polyolefin or an engineering plastic.
[6] A method for stabilizing an organic material, wherein the phosphorous acid compound according to the above [1] is added to an organic material.
[7] The stabilization method according to the above [6], wherein the organic material is a thermoplastic resin.
[8] The stabilization method according to the above [7], wherein the thermoplastic resin is a polyolefin or an engineering plastics.
[9] A stabilized organic material composition containing an organic material, and the phosphorous acid compound according to the above [1].
[10] The composition according to the above [9], wherein the organic material is a thermoplastic resin.
[11] The composition according to the above [10], wherein the thermoplastic resin is a polyolefin or an engineering plastics.

Effect of the Invention

The phosphorous acid compound of the present invention is superior in improvement of heat stability and oxidation stability of organic materials such as thermoplastic resins.

DESCRIPTION OF EMBODIMENTS

The present invention provides a phosphorous acid compound represented by formula (I):

[Chemical Formula 3]

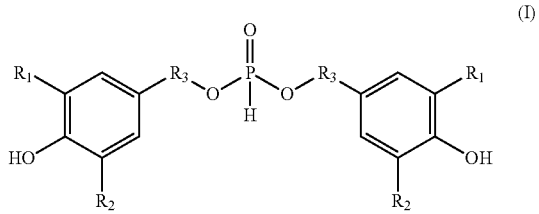

(I)

wherein $R_1$ represents a $C_{1-8}$ alkyl group, a $C_{5-8}$ cycloalkyl group, a $C_{6-12}$ alkyl cycloalkyl group, a $C_{7-12}$ aralkyl group or a $C_{6-12}$ aryl group; $R_2$ represents a hydrogen atom or a $C_{1-3}$ alkyl group; and $R_3$ represents a $C_{3-25}$ alkylene group. Symbols in the above formula (I) will be described.

Examples of the $C_{1-8}$ alkyl group represented by $R_1$ in the formula (I) include, for example, a methyl group, an ethyl group, an n-propyl group, an i-propyl group, an n-butyl group, an i-butyl group, a sec-butyl group, a t-butyl group, a t-pentyl group, an i-octyl group, a t-octyl group, a 2-ethylhexyl group, and the like.

Examples of the $C_{5-8}$ cycloalkyl group represented by $R_1$ in the formula (I) include, for example, a cyclopentyl group, a cyclohexyl group, a cycloheptyl group, a cyclooctyl group, and the like.

Examples of the $C_{6-12}$ alkyl cycloalkyl group represented by $R_1$ in the formula (I) include, for example, a 1-methylcyclopentyl group, a 1-methylcyclohexyl group, a 1-methyl-4-i-propylcyclohextyl group, and the like.

Examples of the $C_{7-12}$ aralkyl group represented by $R_1$ in the formula (I) include, for example, a benzyl group, an α-methylbenzyl group, an α,α-dimethylbenzyl group, and the like.

Examples of the $C_{6-12}$ aryl group represented by $R_1$ in the formula (I) include, for example, a phenyl group, a tolyl group, and the like.

The t-butyl group is preferred as the $C_{1-8}$ alkyl group represented by $R_1$.

Examples of the $C_{1-3}$ alkyl group represented by $R_2$ in the formula (I) include, for example, a methyl group, an ethyl group, an n-propyl group, and an i-propyl group. The methyl group is preferred as $R_2$.

$R_3$ in the formula (I) represents a $C_{3-25}$ alkylene group.

Examples of the $C_{3-25}$ alkylene group include, for example, a propylene group, a tolymethylene group, a tetramethylene group, a pentamethyllene group, a hexamethylene group, a heptamethylene group, an octamethylene group, a nonamethylene group, a decamethylene group, an undecamethylene group, a dodecamethylene group, a tetradecamethylene group, a hexadecamethylene group, an octadecamethylene group, an icosamethylene group, a henicosamethylene group, a docosamethylene group, a tetradocosamethylene group, a pentadocosamethylene group, and the like.

$R_3$ in the formula (I) is preferably a propylene group, a tolymethylene group, a tetramethylene group, or a pentamethylene group.

A phosphorous acid compound represented by the formula (I) can be produced, for example, by reacting a phenol compound represented by formula (II):

[Chemical Formula 4]

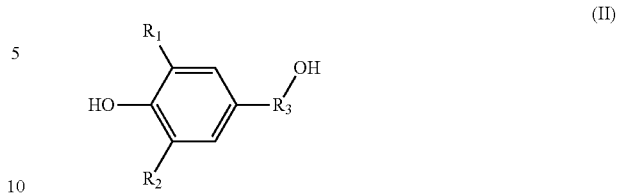

(II)

wherein $R_1$, $R_2$, and $R_3$ are as defined above, with a phosphorus trihalide.

Examples of the phosphorus trihalide include, for example, phosphorus trichloride, phosphorus tribromide, and the like. In particular, phosphorus trichloride is preferably used.

When the phenol compound shown by the above formula (II) is reacted with the phosphorus trihalide, the reaction can also be promoted by the co-presence of dehydrohalogenation agents such as amines, pyridines, pyrrolidines, and amides, or hydroxides of alkali or alkaline-earth metals. In order to promote the reaction, one kind of dehydrohalogenation agent or hydroxide of an alkali metal or an alkaline-earth metal may be singly used, or two or more of them may be used in combination.

Any of primary, secondary, and tertiary amines may be used as the amines. Examples thereof include, for example, t-butylamine, t-pentylamine, t-hexylamine, t-octylamine, di-t-butylamine, di-t-pentylamine, di-t-hexylamine, di-t-octylamine, trimethylamine, triethylamine, N,N-diisopropylethylamine, N,N-dimethylaniline, N,N-diethylaniline, and the like. As the amines, triethylamine is preferably used from the viewpoint that the reaction is easily promoted. Examples of the pyridines include, for example, pyridine, picoline, and the like. Pyridine is preferably used. Examples of the pyrrolidines include, for example, 1-methyl-2-pyrrolidine, and the like. Examples of the amides include, for example, N,N-dimethylformamide, N,N-dimethylacetamide, and the like. N,N-dimethylformamide is preferably used. The above-described dehydrohalogenation agents are preferred since the above reaction can be promoted by forming a salt with a hydrogen halide formed by reacting a phenol compound shown by the formula (II) with a phosphorus trihalide. Furthermore, since the salt formed precipitates, it is also preferable in that the salt can be easily removed by filtration.

Examples of the hydroxides of the alkali metal or alkaline-earth metal include, for example, sodium hydroxide, calcium hydroxide, and the like. Sodium hydroxide is preferably used.

The reaction is usually carried out in an organic solvent. The organic solvent is not particularly limited as long as it does not inhibit the reaction, for example, aromatic hydrocarbons, aliphatic hydrocarbons, oxygen-containing hydrocarbons, halogenated hydrocarbons, and the like are given. The reaction may be carried out in one kind of organic solvent, or may be carried out in a mixed solvent of two or more kinds of organic solvents, or may be carried out in a mixed solvent of the said organic solvent and another solvent.

Examples of the aromatic hydrocarbons include, for example, benzene, toluene, xylene, ethylbenzene, and the like. Examples of the aliphatic hydrocarbons include, for example, n-hexane, n-heptane, n-octane, and the like. Examples of the oxygen-containing hydrocarbons include, for example, diethyl ether, dibutyl ether, tetrahydrofuran, 1,4-dioxane, and the like. Examples of the halogenated hydrocarbons include, for example, chloroform, carbon tetrachloride, monochlorobenzene, dichloromethane, 1,2-dichloroethane, dichlorobenzene, and the like.

In a method for producing a phosphorous acid compound shown by the formula (I), usually, a compound shown by the formula (II) is first reacted with a phosphorus trihalide. By this reaction, a reaction mixture containing a compound shown by formula (V):

[Chemical Formula 5]

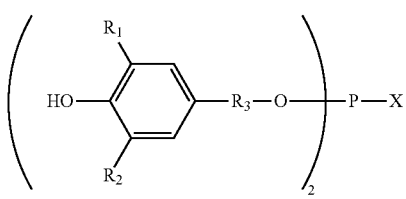

(V)

wherein $R_1$, $R_2$, and $R_3$ are as defined above; X represents a halogen atom, is obtained.

The phosphorus trihalide is preferably used in an amount of about 1-1.1 molar times, and more preferably in an amount of about 1-1.05 molar times the amount of the phenol compound shown by the formula (II). When the dehydrohalogenation agent is used, the dehydrohalogenation agent is preferably used in an amount of about 0.05-2.4 molar times, more preferably in an amount of about 2-2.1 molar times the amount of the phosphorus trihalide. This reaction is usually carried out under an atmosphere of an inert gas, such as nitrogen.

The reaction of the phenol compound shown by the formula (II) with the phosphorus trihalide is usually carried out at a temperature from about −10 to 200° C.

After the reaction of the phenol compound shown by the formula (II) with the phosphorus trihalide, the reaction mixture containing the compound shown by the formula (V) is obtained. It is preferred to add water and the like to the reaction mixture so that a halide as a by-product and a remaining unreacted halide are deactivated. On this occasion, the compound shown by the formula (V) is hydrolyzed so that the phosphorous acid compound of the present invention shown by the formula (I) is produced. Furthermore, without the deactivation step of deactivating the halide by adding water and the like, the compound shown by the formula (V) is hydrolyzed by moisture and the like in the air during post-treatment such as crystallization or column chromatography, so that the compound of the present invention shown by the formula (I) can be obtained.

The phosphorous acid compound of the present invention shown by the formula (I) may be isolated by performing suitable post-treatment such as crystallization or column chromatography as necessary. As described above, by performing the post-treatment such as crystallization or column chromatography using the reaction mixture containing the compound shown by the formula (V) as such, the compound shown by the formula (V) may be hydrolyzed to obtain the phosphorous acid compound of the present invention shown by the formula (I) along with isolation of the phosphorous acid compound of the present invention shown by the formula (I). This post-treatment does not require an atmosphere of an inert gas, and may be carried out in an air atmosphere.

Examples of the phosphorous acid compound shown by the formula (I) include, for example, bis[3-(3-t-butyl-4-hydroxy-5-methylphenyl)propyl]phosphonate, bis[4-(3-t-butyl-4-hydroxy-5-methylphenyl)butyl]phosphonate, bis[5-(3-t-butyl-4-hydroxy-5-methylphenyl)pentyl]phosphonate, bis[10-(3-t-butyl-4-hydroxy-5-methylphenyl)decyl]phosphonate, bis[25-(3-t-butyl-4-hydroxy-5-methylphenyl)pentacosyl]phosphonate, and the like. Among these compounds, bis[3-(3-t-butyl-4-hydroxy-5-methylphenyl)propyl]phosphonate is preferred.

The phenol compound shown by the formula (II) used in the production method of the present invention can be produced, for example, by allowing an unsaturated alcohol to act on a phenol compound in the presence of a base in accordance with JP 3915333 B or JP 4013810 B.

Examples of the base include, for example, alkali metals such as lithium, hydroxides, hydrides, carbonates, alkoxides, amides of alkali metals, and alkaline-earth metals such as calcium, hydroxides, hydrides, carbonates, alkoxides, amides of alkaline-earth metals, and the like. The amount of the base used is usually about 0.01-1 molar times the amount of the phenol compound shown, for example, by the following formula (III).

Examples of the phenol compound include, for example, a compound shown by the following formula (III):

[Chemical Formula 6]

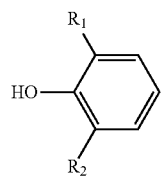

(III)

wherein $R_1$ and $R_2$ are as defined above.

Examples of the unsaturated alcohol include, for example, a compound shown by the following formula (IV):

[Chemical Formula 7]

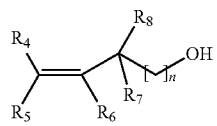

(IV)

$R_4$, $R_5$, $R_6$, $R_7$ and $R_8$ are each independently a hydrogen atom or a $C_{1-8}$ alkyl group, and n represents an integer of 0-22. The compound shown by the formula (IV) has a carbon number of 3-25.

The amount of the unsaturated alcohol used is usually about 0.1-10 molar times the amount of the phenol compound shown, for example, by the formula (III).

When the base, the phenol compound, and the unsaturated alcohol compound are charged simultaneously and reacted, usually, a reaction system is sealed, and they are reacted at a boiling point or more of the unsaturated alcohol compound. The reaction temperature is usually about 100-300° C.

The reaction is carried out in the presence or absence of a reaction solvent. Examples of the solvent include aromatic hydrocarbon solvents such as benzene, ether solvents such as diethyl ether, aliphatic hydrocarbon solvents such as n-hexane, or alcohol solvents such as n-butyl alcohol can be used. The reaction solvent may be a single solvent or a mixed solvent. The amount used when the solvent is used is usually about 0.1-5 times the mass of the phenol compound shown by the formula (III), for example.

Examples of the phenol compound shown by the formula (II) include, for example, 2-t-butyl-4-(hydroxymethyl)-6-methylphenol, 2-t-butyl-4-(2-hydroxyethyl)-6-methylphenol, 2-t-butyl-4-(3-hydroxypropyl)-6-methylphenol, 2-t-butyl-4-(4-hydroxybutyl)-6-methylphenol, 2-t-butyl-4-(5-hydroxypenyl)-6-methylphenol, 2-t-butyl-4-(10-hydroxydecyl)-6-methylphenol, 2-t-butyl-4-(25-hydroxypentacosyl)-6-methylphenol, and the like.

Containing amines, an acid-binding metal salt and the like in the phosphorous compound of the present invention shown by the formula (I) can also improve hydrolysis resistance of the phosphorous acid compound.

Examples of such amines include, for example, trialkanolamines such as triethanolamine, tripropanolamine, and tri-i-propanolamine; dialkanolamines such as diethanolamine, dipropanolamine, di-i-propanolamine, tetraethanolethylenediamine, and tetra-i-propanolethaylenediamine; monoalkanolamines such as dibutylethanolamine and dibutyl-i-propanolamine; aromatic amines such as 1,3,5-trimethyl-2,4,6-triazine; alkylamines such as dibutylamine, piperidine, 2,2,6,6-tetramethylpiperidine, and 4-hydroxy-2,2,6,6-tetramethylpiperidine; and polyalkylenepolyamines such as hexamethylenetetramine, triethylenediamine, triethylenetetramine, and tetraethylenepentamine, a hindered amine light stabilizer described below and the like.

Furthermore, long-chain aliphatic amines described in JP S61-63686 A, compounds containing a steric hindered amine group described in JP H6-329830 A, hindered piperidinyl light stabilizers described in JP H7-90270 A, and organic amines described in JP H7-278164 A can also be used.

The use ratio of the amines to the phosphorous acid compound is usually about 0.01-25 mass % based on the total amount of the phosphorous acid compound shown by the formula (I).

Examples of the acid-binding metal salt include hydrotalcites and the like. Examples of the hydrotalcites include, for example, double-salt compounds shown by the following formula.

$$M^{2+}_{1-x}\cdot M^{3+}_{x}\cdot (OH^-)_2\cdot (A^{n-})_{x/n}\cdot pH_2O$$

wherein $M^{2+}$ represents Mg, Ca, Sr, Ba, Zn, Pb, Sn and/or Ni, $M^{3+}$ represents Al, B or Bi, n represents a numerical value of 1-4, x represents a numerical value of 0-0.5, and p represents a numerical value of 0-2. $A^{n-}$ represents an anion having a valence of n. Here, specific examples of the anion shown by $A^{n-}$ having a valence of n include, for example, $OH^-$, $Cl^-$, $Br^-$, $I^-$, $ClO_4^-$, $HCO_3^-$, $C_6H_5COO^-$, $CO_3^{2-}$, $SO_4^{2-}$, $-OOCCOO-$, $(CHOHCOO)_2^{2-}$, $C_2H_4(COO)_2^{2-}$, $(CH_2COO)_2^{2-}$, $CH_3CHOHCOO^-$, $SiO_3^{2-}$, $SiO_4^{4-}$, $Fe(CN)_6^{4-}$, $BO_3^{3-}$, $PO_3^{3-}$, $HPO_4^{2-}$, and the like.

Among the hydrotalcites represented by the above formula, the more preferred are hydrotalcites represented by the following formula.

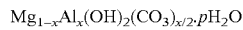

$$Mg_{1-x}Al_x(OH)_2(CO_3)_{x/2}\cdot pH_2O$$

wherein x and p are as defined above.

The hydrotalcites may be natural materials or synthetic products. They can be used irrespective of their crystal structures and crystal grain diameters.

Furthermore, ultrafine zinc oxides described in JP H6-329830 A, inorganic compounds described in JP H7-278164 A, and the like can also be used as the acid-binding metal salts.

The use ratio of the acid-binding metal salt to the phosphorous acid compound is usually about 0.01-25 mass % based on the total amount of the phosphorous acid compound shown by the formula (I).

Containing the phosphorous acid compound of the present invention shown by the formula (I) in the organic material reduces heat deterioration and oxidation deterioration of the organic material so that the organic material can be stabilized. Therefore, the phosphorous acid compound of the present invention is suitable as an active ingredient of a stabilizer for organic materials.

The present invention also provides a stabilizer for an organic material containing the phosphorous acid compound of the present invention shown by the formula (I), a method for stabilizing an organic material in which the phosphorous acid compound of the present invention shown by the formula (I) is added to the organic material, and a stabilized composition containing the organic material and the phosphorous acid compound of the present invention shown by the formula (I). In these embodiments, one kind of phosphorous acid compound shown by the formula (I) may be used as the phosphorous acid compound of the present invention shown by the formula (I), or two or more kinds of phosphorous acid compounds shown by the formula (I) may also be used in combination.

Examples of the organic material which can be stabilized by the phosphorous acid compound of the present invention include, for example, the following materials. However, they are not limited to these organic materials. The organic material may be one kind of organic material, or a mixture of two or more kinds of organic materials.

(1) Polyethylene, for example, high density polyethylene (HD-PE), low density polyethylene (LD-PE), linear low density polyethylene (LLDPE),
(2) polypropylene,
(3) methylpentene polymer,
(4) EEA (ethylene/ethyl acrylate copolymer) resin
(5) ethylene/vinyl acetate copolymer resin
(6) polystyrenes, for example, polystyrene, poly (p-methylstyrene), poly (α-methylstyrene),
(7) AS (acrylonitrile/styrene copolymer) resin,
(8) ABS (acrylonitrile/butadiene/styrene copolymer) resin,
(9) AAS (special acrylic rubber/acrylonitrile/styrene copolymer) resin,
(10) ACS (acrylonitrile/chlorinated polyethylene/styrene copolymer) resin,
(11) chlorinated polyethylene, polychloroprene, chlorinated rubber,
(12) polyvinyl chloride, polyvinilidene chloride,
(13) methacrylic resin,
(14) ethylene/vinyl alcohol copolymer resin,
(15) fluorine resin,
(16) polyacetal,
(17) grafted polyphenylene ether resin and polyphenylene sulfide resin,
(18) polyurethane,
(19) polyamide,
(20) polyester resin, for example, polyethylene terephthalate, polybutylene terephthalate,
(21) polycarbonate,
(22) polyacrylate,

(23) polysulfone, polyether ether ketone, polyether sulfone,
(24) thermoplastic resins such as aromatic polyester resin,
(25) epoxy resin,
(26) diallyl phthalate prepolymer,
(27) silicone resin,
(28) unsaturated polyester resin,
(29) acrylic modified benzoguanamine resin,
(30) benzoguanamine/melamine resin,
(31) thermosetting resin such as urea resin,
(32) polybutadiene,
(33) 1,2-polybutadiene,
(34) polyisoprene,
(35) styrene/butadiene copolymer,
(36) butadiene/acrilonitrile copolymer,
(37) ethylene/propylene copolymer,
(38) silicone rubber,
(39) epichlorohydrin rubber,
(40) acrylic rubber,
(41) natural rubber,
(42) chlorinated rubber paint,
(43) polyester resin paint,
(44) urethane resin paint,
(45) epoxy resin paint,
(46) acrylic resin paint,
(47) vinyl resin paint,
(48) aminoalkyd resin paint,
(49) alkyd resin paint,
(50) nitrocellulose resin paint,
(51) oil paint,
(52) wax,
(53) lubricant, and the like.

Among others, they are preferably used for thermoplastic resins, in particular polyolefins such as polyethylene, for example, HD-PE, LD-PE, LLDPE, and polypropylene; engineering plastics such as polyamide, polyethyleneterephthalate, polybutyleneterephthalate, and polycarbonate.

The polyolefins are not particularly limited. For example, they may be those obtained by radical polymerization, or produced by polymerization using a catalyst containing a metal of group IVb, Vb, VIb or VIII of the Periodic Table. Examples of the catalyst containing such a metal include metal complexes having one or more ligands, for example, an oxide, a halide, an alcoholate, an ester, an aryl and the like, which are coordinated by a π- or σ-bond. These metal complexes may be metal complexes as such, or may be supported on a substrate such as magnesium chloride, titanium chloride, alumina, or silicon oxide. For the polyolefins, those produced using, for example, a Ziegler-Natta catalyst, a TNZ catalyst, a metallocene catalyst, a Phillips catalyst, or the like are preferably used.

The engineering plastics are also not particularly limited. The polyamide resin may be any polyamide resin as long as it has an amide bond at the polymer chain, and can be molten with heating. Polyamide resins may be produced by any method, and those produced by a method such as condensation reaction of diamines and dicarboxylic acids, condensation reaction of aminocarboxylic acids or ring opening polymerization of lactams are given. Examples of the polyamide resins include nylon 66, nylon 69, nylon 610, nylon 612, poly-bis(p-aminocyclohexyl)methanedodecamide, nylon 46, nylon 6, nylon 12 and copolymers, such as nylon 66/6 as a copolymer of nylon 66 and nylon 6, and nylon 6/12. The polyester resin may be any polyester resin as long as it has an ester bond at the polymer chain, and can be molten with heating. Examples thereof include a polyester obtained by the polycondensation of dicarboxylic acids and dihydroxy compounds. The polyester resin may be a homopolyester or a copolyester. The polycarbonate resin may be any polycarbonate resin as long as it has a carbonate bond at the polymer chain, and can be molten with heating. Examples thereof include a polycarbonate obtained by reacting an aromatic hydroxy compound, or an aromatic hydroxy compound and a small amount of polyhydroxy compound with a carbonate precursor such as phosgene or diphenyl carbonate in the presence of a solvent, an acid receptor and a molecular weight adjustor. The polycarbonate resin may be linear or branched, or may be a copolymer.

When the organic material is stabilized by adding the phosphorous acid compound (I) of the present invention, the content of the phosphorous acid compound of the present invention is usually 5 parts by mass or less, preferably 0.0005 parts by mass or more and 3 parts by mass or less, based on 100 parts by mass of the organic material. Even if it is formulated in an amount exceeding 5 parts by mass, an improved effect which is worth the formulation cannot be obtained.

When the phosphorous acid compound shown by the formula (I) is added to the organic material, if necessary, the organic material may contain other additives such as phenol antioxidants, sulfur antioxidants, phosphorus antioxidants, ultraviolet absorbers, light stabilizers, peroxide scavengers, polyamide stabilizers, hydroxyamines, lubricants, plasticizers, flame retardants, nucleating agents, metal-inactivating agents, antistatic agents, pigments, fillers, antiblocking agents, surfactants, processing aids, foaming agents, emulsifiers, brighteners, neutralizers such as calcium stearate, and hydrotalcite, coloring modifiers such as 9,10-dihydro-9-oxa-10-phosphophenanthrene-10-oxide, auxiliary stabilizers such as benzofurans or indolines described in U.S. Pat. Nos. 4,325,853, 4,338,244, 5,175,312, 5,216,053, 5,252, 643, and 4,316,611, DE-A-4,316,622, DE-A-4,316,876, EP-A-589,839, EP-A-591,102 and the like. These additives may be added to the organic material concurrently with the phosphorous acid compound of the present invention, and may also be added to the organic material in a different stage from that of the phosphorous acid compound of the present invention. As the additives, one kind of additive may be used, and two or more kinds of additives may also be used in combination.

Examples of the phenol antioxidants include, for example, the following:

(1) Examples of alkylated monophenols
2,6-di-t-butyl-4-methylphenol, 2,4,6-tri-t-butylphenol, 2,6-di-t-butylphenol, 2-t-butyl-4,6-dimethylphenol, 2,6-di-t-butyl-4-ethylphenol, 2,6-di-t-butyl-4-n-buylphenol, 2,6-di-t-butyl-4-isobuylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6-(1'-methylheptadecyl-1'-yl)phenol, 2,4-dimethyl-6-(1'-methyltridecyl-1'-yl)phenol and their mixtures, and the like.

(2) Examples of alkylthiomethylphenols
2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol and their mixtures, and the like.

(3) Examples of hydroquinones and alkylated hydroquinones
2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenyl stearate, bis(3,5-di-t-butyl-4-hydroxyphenyl)adipate and their mixtures, and the like.

(4) Examples of tocopherols

α-tocopherol, β-tocopherol, γ-tocopherol, δ-tocopherol and their mixtures, and the like.

(5) Examples of hydroxylated thiodiphenylethers 2,2'-thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), 4,4'-(2,6-dimethyl-4-hydroxyphenyl)disulfide, and the like.

(6) Examples of alkylidenebisphenols and derivatives thereof 2,2'-methylenebis(4-methyl-6-t-butylphenol), 2,2'-methylenebis(4-ethyl-6-t-butylphenol), 2,2'-methylenebis[4-methyl-6-(α-methylcyclohexyl)phenol], 2,2'-methylenebis(4-methyl-6-cyclohexphenol), 2,2'-methylenebis(4-methyl-6-nonylphenol), 2,2'-methylenebis(4,6-di-t-butylphenol), 2,2'-ethylidenebis(4,6-di-t-butylphenol), 2,2'-ethylidenebis(4-isobutyl-6-t-butylphenol), 2,2'-methylenebis[6-(α-methylbenzyl)-4-nonylphenol], 2,2'-methylenebis[4,6-(α,α-dimethylbenzyl)-4-nonylphenol)], 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 2,6-bis(3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, ethyleneglycol bis[3,3-bis-3'-t-butyl-4'-hydroxyphenyl)butyrate], bis(3-t-butyl-4-hydroxy-5-methylphenyl)dicyclopentadiene, bis[2-(3'-t-butyl-2'-hydroxy-5'-methylbenzyl)-6-t-butyl-4-methylphenyl] terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate and their mixtures, and the like.

(7) Examples of O-, N- and S-benzyl derivatives 3,5,3',5'-tetra-t-butyl-4,4'-dihydroxydibenzylether, octadodecyl-4-hydroxy-3,5-dimethylbenzylmercapto acetate, tris(3,5-di-t-butyl-4-hydroxybenzyl)amine, bis(4-t-butyl-3-hydroxy-2,6-dimethylbenzyl)dithioterephthalate, bis(3,5-di-t-butyl-4-hydroxybenzyl)sulfide, isooctyl-3,5-di-t-butyl-4-hydroxybenzylmercapto acetate and their mixtures, and the like.

(8) Examples of hydroxybenzylated malonate derivatives

Dicctadecyl-2,2-bis(3,5-di-t-butyl-2-hydroxybenzyl)malonate, dioctadecyl-2-(3-t-butyl-4-hydroxy-5-methylbenzyl)malonate, didodecylmercaptoethyl-2,2-bis(3,5-di-t-butyl-4-hydroxybenzyl)malonate, bis[4-(1,1,3,3-tetramethylbutyl)phenyl]-2,2-bis(3,5-di-t-butyl-4-hydroxybenzyl)malonate and their mixtures, and the like.

(9) Examples of aromatic hydroxybenzyl derivatives 1,3,5-trimethyl-2,4,6-tris(3,5-di-t-butyl-4-hydroxybenzyl)benzene, 1,4-bis(3,5-di-t-butyl-4-hydroxybenzyl)-2,3,5,6-tetramethylbenzene, 2,4,6-tris(3,5-t-butyl-4-hydroxybenzyl)phenol and their mixtures, and the like.

(10) Examples of triazine derivative 2,4-bis(n-octylthio)-6-(4-hydroxy-3,5-di-t-butylanilino)-1,3,5-triazine, 2-n-octylthio-4,6-bis(4-hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3,5-di-t-butyl-4-phenoxy)-1,3,5-triazine, tris(4-t-butyl-3-hydroxy-2,6-dimethylbenzyl)isocyanurate, tris(3,5-di-t-butyl-4-hydroxybenzyl)isocyanurate, 2,4,6-tris(3,5-di-t-butyl-4-hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl)isocyanurate, tris[2-(3',5'-di-t-butyl-4'-hydroxycinnamoyloxy)ethyl]isocyanurate and their mixtures, and the like.

(11) Examples of benzyl phosphonate derivatives

Dimethyl-3,5-di-t-butyl-4-hydroxybenzyl phosphonate, diethyl-3,5-di-t-butyl-4-hydroxybenzyl phosphonate, dioctadecyl-3,5-di-t-butyl-4-hydroxybenzyl phosphonate, dioctadecyl-5-t-butyl-4-hydroxy-3-methylbenzyl phosphonate, calcium salt of 3,5-di-t-butyl-4-hydroxybenzyl phosphonic acid monoesters and their mixtures, and the like.

(12) Examples of acylaminophenol derivatives 4-hydroxylauraic acid anilide, 4-hydroxystearic acid anilide, octyl-N-(3,5-di-t-butyl-4-hydroxyphenyl)carbamate and their mixtures, and the like.

(13) Examples of esters of β-(3,5-di-t-butyl-4-hydroxyphenyl)propionic acid and the following monohydric or polyhydric alcohols Methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanuarte, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and their mixtures, and the like.

(14) Examples of esters of β-(5-t-butyl-4-hydroxy-3-methyphenyl)propionic acid and the following monohyric or polyhydric alcohols Methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylen glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and their mixtures, and the like.

(15) Examples of esters of β-(3,5-dicyclohexyl-4-hydroxyphenyl)propionic acid and the following monohydric or polyhydric alcohols Methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and their mixtures, and the like.

(16) Examples of esters of 3,5-di-t-butyl-4-hydroxyphenylacetic acid and the following monohydric or polyhydric alcohols Methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and their mixtures, and the like.

(17) Examples of amides of β-(3,5-di-t-butyl-4-hydroxyphenyl)propionic acid

N,N'-bis[3-(3',5'-di-t-butyl-4'-hydroxyphenyl)propionyl] hydrazine, N,N'-bis[3-(3',5'-di-t-butyl-4'-hydroxyphenyl) propionyl]hexamethylenediamine, N,N'-bis[3-(3',5'-di-t-butyl-4'-hydroxyphenyl)propionyl]trimethylenediamine and their mixtures, and the like.

Examples of the sulfur antioxidant include, for example the following.

Dilauryl 3,3'-thiodipropionate, tridecyl 3,3'-thiodipropionate, dimyristyl 3,3'-thiodipropionate, distearyl 3,3'-thiodipropionate, lauryl stearyl 3,3'-thiodipropionate, neopentanetetrayltetrakis(3-lauryl thiopropinate), and the like.

Examples of the phosphorus antioxidants include, for example, the following.

Triphenyl phosphite, tris(nonylphenyl)phosphite, tris(2,4-di-t-butylphenyl)phosphite, trilauryl phosphite, trioctadecyl phosphite, distearyl pentaerythritol diphosphite, diisodecyl pentaerythritol diphosphite, bis(2,4-di-t-butylphenyl)pentaerythritol diphosphite, bis(2,4-di-t-butyl-6-methylphenyl) pentaerythritol diphosphite, bis(2,6-di-t-butyl-4-methylphenyl)pentaerythritol diphosphite, bis(2,4,6-tri-t-butylphenyl) pentaerythritol diphosphite, tristearyl sorbitol triphosphite, tetrakis(2,4-di-t-butylphenyl)-4,4'-diphenylene diphosphonite, 2,2'-methylenebis(4,6-di-t-butylphenyl)2-ethylhexyl phosphite, 2,2'-ethylidenebis(4,6-di-t-butylphenyl)fluoro phosphite, bis(2,4-di-t-butyl-6-methylphenyl)ethyl phosphite, bis(2,4-di-t-butyl-6-methylphenyl)methyl phosphite, 2-(2,4,6-tri-t-butylphenyl)-5-ethyl-5-butyl-1,3,2-oxaphosphorinane, 2,2',2"-nitrilo[triethyl-tris(3,3',5,5'-tetra-t-butyl-1,1'-biphenyl-2,2'-idyl)phosphite, 6-[3-(3-t-butyl-4-hydroxy-5-methylphenyl)propoxy]-2,4,8,10-tetra-t-butyldibenz[d,f][1,3,2]dioxaphosphepine and their mixtures, and the like.

Examples of the ultraviolet absorbers include, for example, the following.

(1) Example of salicylate derivatives

Phenyl salicylate, 4-t-butylphenyl salicylate, 2,4-di-t-butylphenyl 3',5'-di-t-butyl-4'-hydroxybenzoate, 4-t-octylphenyl salicylate, bis(4-t-butylbenzoyl)resorcinol, benzoylresorcinol, hexadecyl 3',5'-di-t-butyl-4'-hydroxybenzoate, octadecyl 3',5'-di-t-butyl-4'-hydroxybenzoate, 2-methyl-4,6-di-t-butylphenyl 3',5'-di-t-butyl-4'-hydroxybenzoate and their mixtures, and the like.

(2) Examples of 2-hydroxybenzophenone derivatives 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone and their mixtures, and the like.

(3) Examples of 2-(2'-hydroxyphenyl)benzotriazoles 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl) benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole, 2-[2'-hydroxy-3',3'-bis (α,α-dimethylbenzyl)phenyl]-2H-benzotriazole, 2-[(3'-t-butyl-2'-hydroxyphenyl)-5'-(2-octyloxycarbonyl)phenyl]-5-chlorobenzotriazole, 2-[3'-t-butyl-5'-[2-(2-ethylhexyloxy) carbonylethyl]-2'-hydroxyphenyl]-5-chlorobenzotriazole, 2-[3'-t-butyl-3'-hydroxy-5'-(2-methoxycarbonylethyl)phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5-(2-octyloxycarbonylethyl)phenyl] benzotriazole, 2-[3'-t-butyl-2'-hydroxy-5'-[2-(2-ethylhexloxy)carbonylethyl]phenyl]benzotriazole, 2-[2-hydroxy-3-(3,4,5,6-tetrahydrophthalimidemethyl)-5-methylphenyl]benzotriazole, 2(3,5-di-t-butyl-2-hydroxyphenyl)-5-chlorobenzotriazole, mixture of 2-(3'-dodecyl-2'-hydroxy-5'-methylphenyl)benzotriazole and 2-[3'-t-butyl-2'-hydroxy-5'-(2-isooctyloxycarbonylethyl) phenyl]benzotriazole, 2,2'-methylenebis[6-(2H-benzotriazol-2-yl)-4-(1,1,3,3-tetramethylbutyl)phenol, 2,2'-methylenebis[4-t-butyl-6-(2H-benzotriazol-2-yl)phenol], condensate of poly(3-11) (ethylene glycol) and 2-[3'-t-butyl-2'-hydroxy-5'-(2-methoxycarbonylethyl)phenyl]benzotriazole, condensate of poly (3-11) (ethylene glycol) and methyl 3-[3-(2H-benzotriazol-2-yl)-5-t-butyl-4-hydroxyphenyl] propionate, 2-ethylhexyl 3-[3-t-butyl-5-(5-chloro-2H-benzotriazol-2-yl)-4-hydroxyphenyl]propionate, octyl 3-[3-t-butyl-5-(5-chloro-2H-benzotriazol-2-yl)-4-hydroxyphenyl] propionate, methyl 3-[3-t-butyl-5-(5-chloro-2H-benzotriazol-2-yl)-4-hydroxyphenyl]propionate, 3-[3-t-butyl-5-(5-chloro-2H-benzotriazol-2-yl)-4-hydroxyphenyl] propionic acid and their mixtures, and the like.

Examples of the light stabilizers include, for example, the following.

(1) Examples of the hindered amine light stabilizers

Bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl)sebacate, bis(1,2,2,6,6-pantamethyl-4-piperidyl)2-(3,5-di-t-butyl-4-hydroxybenzyl)-2-butylmalonate, bis(1-acrolyl-2,2,6,6-tetramethyl-4-piperidyl) 2,2-bis(3,5-di-t-butyl-4-hydroxybenzyl)-2-butylmalonate, bis(1,2,2,6,6-pentamethyl-4-piperidyl)decanedioate, 2,2,6,6-tetramethyl-4-piperidyl methacrylate, 4[3-(3,5-di-t-butyl-4-hydroxyphenyl)propionyloxy]-1-[2-(3-(3,5-di-t-butyl-4-hydroxyphenyl)propionyloxy ethyl]-2,2,6,6-tetramethylpiperidine, 2-methyl-2-(2,2,6,6-tetramethyl-4-piperidyl)amino-N-(2,2,6,6-tetramethyl-4-piperidyl) propionamide, tetarkis(2,2,6,6-tetramethyl-4-piperidyl)1,2,3,4-butanetetracarboxylate, tetrakis(1,2,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarbxylic acid and 2,2,6,6-tetramethyl-4-piperidinol and 1-tridecanol, mixed esterified product of 1,2,3,4-butanetetracarbxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetarmethyl-4-piperidinol and 3,9-bis (2-hydroxy-1,1-dimethyethyl)-2,4,8,10-tetraoxaspiro [5.5] undecane, polycondensate of dimethyl succinate and 1-(2-hydroxyethyl)4-hydroxy-2,2,6,6-tetramethylpiperidine, poly[(6-morpholino-1,3,5-triazin-2,4-diyl)((2,2,6,6-tetramethyl-4-piperidyl)imino)hexamethylene ((2,2,6,6-tetramethyl-4-piperidyl)imino)], poly (6-(1,1,3,3-tetramethylbutyl)imino-1,3,5-triazin-2,4-diyl ((2,2,6,6-tetramethyl-4-piperidyl)imino)hexanmethylene ((2,2,6,6-tetremethyl-4-piperidyl)imino)], polycondensate of N,N'-bis(2,2,6,6-tetramethyl-4-piperidyl)hexamethylenediamine and 1,2-dibromoethane, N,N',4,7-tetrakis[4,6-bis(N-butyl-N-(2,2,6,6-tetramethyl-4-piperidyl)amino)-1,3,5-triazin-2-yl]-4,7- diazadecane-1,10 diamine, N,N',4-tris[4,6-bis(N-butyl-N-(2,2,6,6-tetramethyl-4-piperidyl)amino)-1,3,5-triazin-2-yl]-4,7-diazadecane-1,10 diamine, N,N',4,7-tetrakis[4,6-bis(N-butyl-N-(1,2,2,6,6-pentamethyl-4-piperidyl)amino)-1,3,5-triazin-2-yl]-4,7-diazadecane-1,10 diamine, N,N',4-tris[4,6-bis(N-butyl-N-(1,2,2,6,6-pentamethyl-4-piperidyl)amino)-1,3,5-triazin-2-y]-4,7-diazadecane-1,10 diamine and their mixtures, and the like.

(2) Examples of acrylate light stabilizers

Ethyl α-cyano-β,β-dipheylacrylate, isooctyl α-cyano-β,β-diphenylacrylate, methyl α-carbomethoxycinnamate, methyl α-cyano-β-methyl-p-methyoxycinnamate, butyl α-cyano-β-methyl-p-methoxycinnamate, methyl α-carbomethoxy-p-methyoxycinnamate, N-(β-carbomethoxy-β-cyanovinyl)-2-methylindoline and their mixtures, and the like.

(3) Examples of nickel light stabilizers

Nickel complex of 2,2'-thiobis-[4-(1,1,3,3-tetremethylbutyl)phenol], nickel dibutyldithiocarbamate, nickel salts of monoalkyl esters, nickel complex of ketoxime and their mixtures, and the like.

(4) Examples of oxamide light stabilizers 4,4'-dioctyloxyoxanilide, 2,2'-diethoxyoxanilide, 2,2'-dioctyloxy-5,5'-di-t-butylanilide, 2,2'-didodecyloxy-5,5'-di-t-butylanilide, 2-ethoxy-2'-ethyloxanilide, N,N'-bis(3-dimethylaminopropyl)oxamide, 2-ethoxy-5-t-butyl-2'-ethoxyanilide, 2-ethoxy-5,4'-di-t-butyl-2'-ethyloxanilide and their mixtures, and the like.

(5) Examples of 2-(2-hydroxyphenyl)-1,3,5-triazine light stabilizers 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-[(2,4-dihydroxyphenyl-4,6-bis(2,4-dimethylphenyl]-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1,3,5-triazine and their mixtures, and the like.

Examples of the metal inactivating agent include, for example, the following.

N,N'-diphenyloxamide, N-salicylal-N'-salicyloylhydrazine, N,N'-bis(salicyloyl)hydrazine, N,N'-bis(3,5-di-t-butyl-4-hydroxyphenylpropionyl)hydrazine, 3-salicyloylamino-1,2,4-triazole, bis(benzylidene)oxalyl dihydrazide, oxalinide, isophthaloyl dihydrazide, sebacoylbisphenyl hydrazie, N,N'-bis(salicyloyl)oxalyl dihydrazide, N,N'-bis(salicyloyl)thiopropionyl dihydrazide and mixtures thereof, and the like.

Examples of the peroxide scavengers include, for example, esters of β-thiodipropionic acid, mercaptobenzimidazole, zinc salt of 2-mercaptobenzimidazole, zinc salt of dibutyldithiocarbamic acid, dioctadecyl disulfide, pentaerythritol tetrakis(β-dodecylmercapto)propionate and their mixtures, and the like.

Examples of the polyamide stabilizers include, for example, copper or divalent manganese salts of iodide or phosphorus compounds and their mixtures, and the like.

Examples of the hydroxyamines include, for example, N,N-dibenzylhydroxyamine, N,N-diethylhydroxyamine, N,N-dioctylhydroxyamine, N,N-dilaurylhydroxyamine, N,N-ditetradecylhydroxyamine, N,N-dihexadecylhydroxyamine, N,N-dioctadecylhydroxyamine, N-hexadecyl-N-octadecylhydroxyamine, N-heptadecyl-N-octadecylhydroxyamine and their mixtures, and the like.

Examples of neutralizers include, for example, calcium stearate, zinc stearate, magnesium stearate, hydrotalcite such as basic magnesium aluminum hydroxy carbonate hydrate, melamine, amine, polyamide, polyurethane and their mixtures, and the like.

Examples of the lubricants include, for example, aliphatic hydrocarbons such as paraffin and wax, higher fatty acids having 8 to 22 carbon atoms, metal (Al, Ca, Mg, Zn) salts of higher fatty acids having 8 to 22 carbon atoms, aliphatic alcohols having 8 to 22 atoms, polyglycol, esters of higher fatty acids having 4 to 22 carbon atoms and aliphatic monovalent alcohols having 4 to 18 carbon atoms, higher aliphatic amides having 8 to 22 carbon atoms, silicone oil, rosin derivatives, and the like.

Examples of the nucleating agent include, for example, the following. Sodium 2,2'-methylenebis(4,6-di-t-butylphenyl)phosphate, [phosphoric acid-2,2'-methylenebis(4,6-di-t-butylphenyl)] dihydroxyaluminum, bis[phosphoric acid-2,2'-methylenebis(4,6-di-t-butylphenyl)]dihydroxyaluminum, tris [phosphoric acid-2,2'-methylenebis(4,6-di-t-butylphenyl)]aluminum, sodium bis(4-t-butylphenyl)phosphate, benzoic acid metal salts such as sodium benzoate, aluminum p-t-butylbenzoate, 1,3:2,4-bis(O-benzylidene)sorbitol, 1,3:2,4-bis (O-methylbenzylidene)sorbitol, 1,3:2,4-bis(O-ethylbenzylidene)sorbitol, 1,3-O-3,4-dimethylbenzylidene-2,4-O-benzylidenesorbitol, 1,3-O-benzylidene-2,4-O-3,4-dimethylbenzylidenesorbitol, 1,3:2,4-bis-(O-3,4-dimethylbenzylidene)sorbitol, 1,3-O-p-chlorobenezylidene-2,4-O-3,4-dimethylbenzilidene sorbitol, 1,3-O-3,4-dimethylbenzilidene-2,4-O-p-chlorobenzilidene sorbitol, 1,3:2,4-bis(O-p-chlorobenzilidene)sorbitol and their mixtures, and the like.

Examples of the fillers include, for example, calcium carbonate, silicate, glass fiber, asbestos, talc, kaoline, mica, barium sulfate, carbon black, carbon fiber, zeolite and their mixtures, and the like.

Among these additives, those which are preferably used include phenol antioxidants, phosphorus antioxidants, ultraviolet absorbers, hindered amine light stabilizers, peroxide scavengers and neutralizers.

Examples of the particularly preferred phenol antioxidants include the following compounds. As the phenol antioxidants, the following compounds may be singly used, and two or more kinds of them may also be used in combination.

2,6-di-t-butyl-4-methylphenol, 2,4,6-tri-t-butylphenol, 2,4-dioctylthiomethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis(4-ethyl-6-t-butylphenol), 2,2'-methylenebis[4-methyl-6-(α-methylcyclohexlphenol)], 2,2'-methylenebis(4-methyl-6-cyclohexylphenol), 2,2'-methylenebis(4-methyl-6-cyclohexylphenol), 2,2'-methylenebis(4,6-di-t-butylphenol), 2,2'-ethylidenebis(4,6-di-t-butylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1'-bis(4-hydroxyphenyl)cyclohexane, 1,1-bis(5-t-butyl-4-hydroxy-2-methylphenyl)butane, 1,1,3-tris(5-t-butyl-4-hydroxy-2-methylphenyl)butane, ethylene glycol bis[3,3-bis-3'-t-butyl-4'-hydroxyphenyl)butyrate], 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, 2,4,6-tris(3,5-di-t-butyl-4-phenoxy)-1,3,5-triazine, tris(4-t-butyl-3-hydroxy-2,6-dimethylbenzyl)isocyanurate, bis(3, 5-di-t-butyl-4-hydroxybenzyl)isocyanurate, tris 2-[(3',5'-di-t-butyl-4'-hydroxycinnamoyloxy)ethyl)]isocyanurate, diethyl-3,5-di-t-butyl-4-hydroxybenzyl phosphonate, di-n-octadecyl-3,5-di-t-butyl-4-hydroxybenzyl phosphonate, calcium salt of 3,5-di-t-butyl-4-hydroxybenzylphosphonic acid monoester, n-octadecyl 3-(3,5-di-t-butyl-4-hydroxyphenyl) propionate, neopentanetetrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butyl-4-hydroxy-3-methylcinnamate), 3,9-bis[2-(3-(3-t-butyl-4-hydroxy-5-methylphenyl)propionyloxy)-1,1-dimethylethyl]-2,4,4,10-tetraoxaspiro[5.5]undecane, N,N'-bis[3-(3',5'-di-t-butyl-4'-hydroxyphenyl)propionyl] hydrazine, N,N'-bis[3-(3',5'-di-t-butyl-4'-hydroxyphenyl) propionyl]hexamethylenediamine, and the like.

Examples of the particularly preferred phosphorus antioxidants include the following compounds. As the phosphorus antioxidants, the following compounds may be singly used, and two or more kinds of them may also be used in combination.

Tris(nonylphenyl)phosphite, tris (2,4-di-t-butylphenyl) phosphite, distearyl pentaerythritol diphosphite, bis(2,4-di-t-butylphenyl)pentaerythritol diphosphite, bis(2,4-di-t-butyl-6-methylphenyl)pentaerythritol disphosphite, bis(2,6-di-t-butyl-4-methylphenyl)pentaerythritol diphosphite, tetrakis (2,4-di-t-butylphenyl)-4,4'-diphenylenediphosphonite, 2,2'-methylenebis(4,6-di-t-butylphenyl) 2-ethylhexyl phosphite, 2,2'-ethylidenebis(4,6-di-t-butylphenyl) fluorophosphite, bis (2,4-di-t-butyl-6-methylphenyl)ethylphosphite, 2-(2,4,6-tri-t-butylphenyl)-5-ethyl-5-butyl-1,3,2-oxaphospholinane, 2,2',2''-nitrilo[triethyl-tris(3,3',5,5'-tetra-t-butyl-1,1'-biphenyl-2,2'-diyl)phosphite, 6-[3-(3-t-butyl-4-hydroxy-5-methylphenyl)propoxy]-2,4,8,10-tetra-t-butyldibenz[d,f][1,3,2] dioxaphosphepine, and the like.

Examples of the particularly preferred ultraviolet absorbers include the following compounds. As the ultraviolet absorbers, the following compounds may be singly used, and two or more kinds of them may also be used in combination.

Phyenyl salicylate, 4-t-butylphenyl salicylate, 2,4-di-t-butylphenyl 3',5'-di-t-butyl-4'-hydroxybenzoate, 4-t-octylphenyl salycilate, 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone, 2-(2-hydroxy-5-methylphenyl) benzotriazole, 2-(3',5'-di-t-butyl-2'-hydroxyphenyl) benzotriazole, 2-(5'-t-butyl-2'-hydroxyphenyl) benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3', 5'-di-t-amyl-2'-hydroxyphenyl)benzotriazole, 2-[2'-hydroxy-3',5'-bis(α,α-dimethylbenzyl)phenyl]-2H-benzotriazole, and the like.

Examples of the particularly preferred light stabilizers include the following compounds. As the light stabilizers, the following compounds may be singly used, and two or more kinds of them may also be used in combination.

Bis(2,2,6,6-tetramethyl-4-piperidyl)sebacate, bis(1,2,2,6, 6-pentamethyl-4-piperidyl)sebacate, bis(N-octoxy-2,2,6,6-tetramethyl-4-piperidyl)sebacate, bis(N-benzyloxy-2,2,6,6-tetarmethyl-4-piperidyl)sebacate, bis(N-cyclohexyloxy-2,2, 6,6-tetramethyl-4-piperidyl)sebacate, bis (1,2,2,6,6-pentamethyl-4-piperidyl) 2-(3,5-di-t-butyl-4-hydroxybenzyl)-2-butylmalonate, bis(1-acryloyl-2,2,6,6-tetramethyl-4-piperidyl) 2,2-bis(3,5-di-t-butyl-4-hydroxybenzyl)-2-butylmalonate, bis(2,2,6,6-tetramethyl-4-piperidyl)succinate, 2,2,6,6-tetramethyl-4-piperidyl methacrylate, 4-[3-(3,5-di-t-butyl-4-hydroxyphenyl)propionyloxy)]-1-[2-(3-(3,5-di-t-butyl-4-hydroxyphenyl)propionyloxy)ethyl]-2,2,6,6-tetramethylpiperidine, 2-methyl-2-(2, 2,6,6-tetramethyl-4-piperidyl)amino-N-(2,2,6,6-tetarmethyl-4-piperidyl)propionamide, tetrakis(2,2,6,6-tetramethyl-4-piperidyl) 1,2,3,4-butanetetracarboxylate, tetrakis(1,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-tetracarboxylic acid and 1,2,2,6,6,-pentamethyl-4-piperidinol and 3,9-bis(2-hydroxy-1,1-dimethylethyl)-2,4,8, 10-tetraoxaspiro [5.5]undecane, mixed esterified product of 1,2,3,4-butanetetracarboxylic acid and 2,2,6,6-tetarmethyl-4-piperidinol and 3,9-bis(2-hydroxy-1,1-dimethylethyl)-2,4, 8,10-tetraoxaspiro [5.5]undecane, polycondensate of dimethyl succinate and 1-(2-hydroxyethyl)-4-hydroxy-2,2,6,6-tetramethylpiperidine, poly[(6-morphonlino-1,3,5-triazin-2, 4-diyl)((2,2,6,6-tetramethyl-4-piperidyl)imino) hexamethylene ((2,2,6,6-tetramethyl-4-piperidyl)imino)], poly[(6-(1,1,3,3-tetramethybutyl)-1,3,5-triazine-2,4-diyl ((2,2,6,6-tetramethyl-4-piperidyl)imino)hexamethylene ((2, 2,6,6-tetramethyl-4-piperidyl)imino)], and the like.

The phosphorous acid compound of the present invention shown by the formula (I) and/or optionally added other additives can be formulated in the organic material using any known method and device for obtaining a homogeneous mixture. For example, when the organic material is a solid polymer, the phosphorous acid compound of the present invention and/or optionally added other additives can be directly dry-blended in the solid polymer. Alternatively, the phosphorous acid compound and/or optionally added other additives can also be added to the organic material in the form of a masterbatch. When the organic material is a liquid polymer, in addition to the aforesaid addition method, the phosphorous acid compound and/or optionally added other additives can also be formulated to the polymer solution during or immediately after polymerization in the form of a solution or a dispersion. On the other hand, when the organic material is a liquid other than the solid polymer, such as oil, in addition to the aforesaid addition method, the phosphorous acid compound and/or optionally added other additives can also be dissolved by direct addition, or the phosphorous acid compounds of the present invention and optionally added other additives can also be added to the organic material in a state in which they are dissolved or suspended in a liquid medium.

The phosphorous acid compound of the present invention shown by the formula (I) exhibits excellent performance as stabilizers for various organic materials, including thermoplastic resins such as polyolefins. The organic material added with the phosphorous compound of the present invention is stable to heat deterioration and oxidation deterioration during production, processing and use to become a high-quality product.

EXAMPLES

The present invention is further described in detail by showing examples. However, it should not be construed that the present invention is limited by them.

Characterization of compounds was performed by mass analysis (High-Mass Measurement), $^1$H-NMR measurement and $^{31}$P-NMR measurement under the following conditions.

[Conditions for Measurement (High-Mass Measurement) of Molecular Weight]

Device: LC="Nexera" manufactured by Shimazu Corporation, Mass Spectrometer="Exactive" manufactured by Thermo Fisher Scientific Inc., Mobile Phase: water with 0.1% formic acid/methanol (1:1), Flow Rate: 0.2 mL/min., Ionization Method: ESI, Ion Polarity: Positive, Scanning Range: m/Z=100-1200

[Conditions for $^1$H-NMR Measurement]

Measurement Nucleus: H nucleus, Resonance Frequency: 500 MHz, Observation Range: 20 ppm, Measurement Temperature: 25.3° C., Solvent for Measurement: CDCl$_3$, Internal Standard Material: tetramethylsilane

[Conditions for $^{31}$P-NMR Measurement]

Measurement Nucleus: P nucleus, Resonance Frequency: 202 MHz, Observation Range: 500 ppm, Measurement Temperature: 25.0° C., Solvent for Measurement: CDCl$_3$, External Standard Material: phosphoric acid Example 1: Production of Phosphorous Acid Compound Shown by Formula (I-1): Bis{3-(3-t-butyl-4-hydroxy-5-methylphenyl)propyl}phosphonate According to the method described in JP 4013810 B, a phenol compound shown by formula (II-1): 3(3-t-butyl-4-hydroxy-5-methylphenyl)propanol was synthesized.

In a flask equipped with a thermometer, a stirrer and a cooling tube, 13.34 g (60 mmol) of the compound shown by the formula (II-1), and 50 mL of dichloromethane were charged, and, under a nitrogen atmosphere, 4.12 g (30 mmol) of phosphorous trichloride was allowed to flow thereinto at 15-29° C. under ice cooling. Subsequently, 6.27 g (62 mmol) of triethylamine was added dropwise at 25-26° C. After the dropwise addition, 25 mL of dichloromethane was added and the mixture was stirred for 3 hours at room temperature. The mixture was subjected to distillation at 40° C. or less under reduced pressure. To the resultant residue, 200 mL of diethyl ether was added to precipitate triethylamine hydrochloride. The precipitated triethylamine hydrochloride was removed by filtration. A filtrate was distilled under reduced pressure at 40° C. or less, and the concentrated residue was purified by silica gel column chromatography. The solvent was distilled off under reduced pressure to obtain 2.91 g of a phosphorous acid compound shown by the formula (I-1).

[Chemical Formula 8]

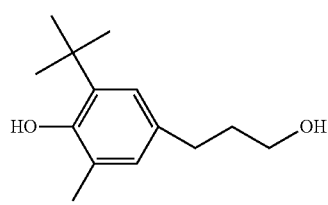

(II-1)

[Chemical Formula 9]

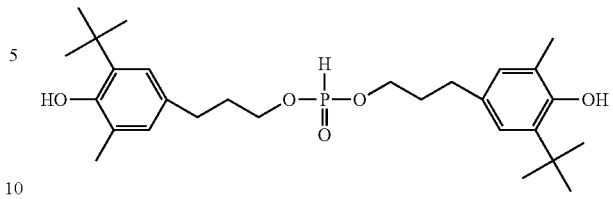

(I-1)

Results of measurement of the phosphorous acid compound shown by the formula (I-1)

$^1$H-NMR

δ=7.52, 6.13 (d, JP-H=695 Hz, 1H, PH), 6.92 (d, J4=2.5 Hz, 2H, Ar—H), 6.80 (d, J4=2.5 Hz, 2H, Ar—H), 5.04 (bs, 2H, OH), 4.09 (t, J3=6.5 Hz, 4H, O—CH$_2$—CH$_2$), 2.60 (t, J3=6.5 Hz, 4H, —CH$_2$-Ph), 2.20 (s, 6H, Ar—CH$_3$), 1.97 (qui, J3=6.5 Hz, 4H, —CH$_2$—CH$_2$—CH$_2$—), 1.40 (s, 18H, C—(CH$_3$)$_3$)

$^{31}$P-NMR:

δ=8.96 ppm

High-Mass:

[M+H]$^+$=m/z 491.2911

[Stabilizing Effect on Polyethylene]

Example 2

To 100 parts by mass of a linear low-density polyethylene ("GA401" manufactured by SUMITOMO CHEMICAL COMPANY, LIMITED) were added 0.10 part by mass of a phosphorous acid compound obtained in Example 1 as an antioxidant and 0.05 part by mass of calcium stearate, and the mixture was dry blended. Then, the resultant blended product was granulated at 190° C. using a 30 mm-diameter single screw extruder to obtain pellets. Thereafter, the pellets were charged in the single screw extruder again to repeat an operation of extruding them 5 times at 230° C. MFR values of the pellets before performing extrusion at 230° C. (0 time), and after extrusion once, three times and five times were measured at 190° C., and 21.18 N (a 2.16 kg load) using a "Melt Indexer L246-3537" manufactured by TECHNO SEVEN CO., LTD. In Table 1, an MFR value for 0 time, and an MFR value after the extrusion operation 5 times are shown. Here, it is known that in the low-density polyethylene, crosslinking proceeds by extrusion leading to deterioration. This phenomenon can be observed as a reduction in the MFR value. Therefore, when the MFR value is maintained without being reduced even if the extrusion operation is repeated, this demonstrates that crosslinking of polyethylene is inhibited, and that polyethylene is high in processing stability.

Comparative Example 1

MFR measurement was performed in the same manner as in Example 2, except that the phosphorous acid compound was not added. The obtained results are shown in Table 1.

TABLE 1

| | MFR Value [g/10 min.] | | |
|---|---|---|---|
| | 0 time | 5 times | 5 times/0 time |
| Example 2 | 2.2 | 1.2 | 0.54 |
| Comp. Example 1 | 1.6 | 0.4 | 0.25 |

[Stabilizing Effect on Polypropylene]

Example 3

To 100 parts by mass of a homopolypropylene ("HS200" manufactured by SUMITOMO CHEMICAL COMPANY, LIMITED) were added 0.10 part by mass of the phosphorous acid compound obtained in Example 1 as the antioxidant and 0.05 part by mass of calcium stearate, and the mixture was dry blended. Then, the resultant blended product was granulated at 230° C. using a 30 mm-diameter single screw extruder to obtain pellets. Thereafter, MFR values of pellets were measured at 230° C., and 21.18 N (a 2.16 kg load) using a "Melt Indexer L246-3537" manufactured by TECHNO SEVEN CO., LTD. The obtained results are shown in Table 2. Here, it is known that decomposition of the polypropylene chain proceeds by extrusion leading to deterioration. This phenomenon can be observed as an increase in the MFR value. Therefore, when the MFR value is maintained without being increased even if the extrusion operation is performed, this demonstrates that decomposition of polypropylene is inhibited, and that polypropylene is high in processing stability.

Comparative Example 2

The MFR measurement was performed in the same manner as in Example 3, except that the phosphorous acid compound was not added. The results obtained are shown in Table 2.

TABLE 2

| | MFR Value [g/10 min.] |
|---|---|
| Example 3 | 3.5 |
| Comp. Example 2 | 9.7 |

The invention claimed is:

1. A phosphorous acid compound represented by formula (I):

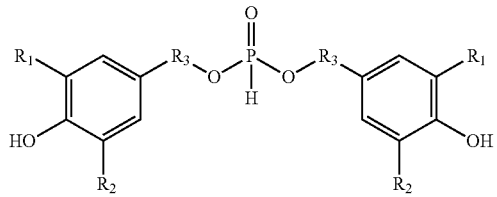

wherein $R_1$ represents a $C_{1-8}$ alkyl group, a $C_{5-8}$ cycloalkyl group, a $C_{6-12}$ alkyl cycloalkyl group, a $C_{7-12}$ aralkyl group or a $C_{6-12}$ aryl group; $R_2$ represents a hydrogen atom or a $C_{1-3}$ alkyl group; and $R_3$ represents a $C_{3-25}$ alkylene group.

2. A method for producing the phosphorous acid compound according to claim 1 by reacting a phenol compound represented by formula (II):

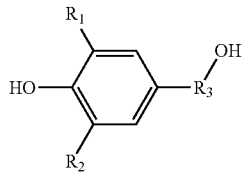

wherein $R_1$, $R_2$, and $R_3$ are as defined above, with a phosphorus trihalide.

3. A stabilizer for an organic material, containing the phosphorous compound according to claim 1.

4. The stabilizer according to claim 3, wherein the organic material is a thermoplastic resin.

5. The stabilizer according to claim 4, wherein the thermoplastic resin is a polyolefin or an engineering plastic.

6. A method for stabilizing an organic material, wherein the phosphorous acid compound according to claim 1 is added to an organic material.

7. The stabilization method according to claim 6, wherein the organic material is a thermoplastic resin.

8. The stabilization method according to claim 7, wherein the thermoplastic resin is a polyolefin or an engineering plastic.

9. A stabilized organic material composition containing an organic material, and the phosphorous acid compound according to claim 1.

10. The composition according to claim 9, wherein the organic material is a thermoplastic resin.

11. The composition according to claim 10, wherein the thermoplastic resin is a polyolefin or an engineering plastic.

* * * * *